United States Patent
Insa Boronat et al.

(10) Patent No.: US 12,257,253 B2
(45) Date of Patent: Mar. 25, 2025

(54) TRIAMTERENE OR NOLATREXED FOR USE IN THE TREATMENT OF PHENYLKETONURIA

(71) Applicant: SOM INNOVATION BIOTECH, S.A., Barcelona (ES)

(72) Inventors: Raúl Insa Boronat, Barcelona (ES); Núria Reig Bolaño, Barcelona (ES); Aileen Ferré Ferré, Barcelona (ES); Óscar Huertas Gambin, Barcelona (ES); Santiago Esteva Gras, Barcelona (ES); Luca Signorile, Barcelona (ES); Gal.la Pericot Mohr, Barcelona (ES)

(73) Assignee: SOM INNOVATION BIOTECH, S.A., Barcelona (ES)

( * ) Notice: Subject to any disclaimer, the term of this patent is extended or adjusted under 35 U.S.C. 154(b) by 827 days.

(21) Appl. No.: 17/430,060

(22) PCT Filed: Feb. 13, 2020

(86) PCT No.: PCT/EP2020/053714
§ 371 (c)(1),
(2) Date: Aug. 11, 2021

(87) PCT Pub. No.: WO2020/165318
PCT Pub. Date: Aug. 20, 2020

(65) Prior Publication Data
US 2022/0133726 A1    May 5, 2022

(30) Foreign Application Priority Data
Feb. 14, 2019  (EP) .................................. 19382102

(51) Int. Cl.
A61K 31/519   (2006.01)
A61K 31/517   (2006.01)
A61K 45/06    (2006.01)

(52) U.S. Cl.
CPC .......... *A61K 31/519* (2013.01); *A61K 31/517* (2013.01); *A61K 45/06* (2013.01)

(58) Field of Classification Search
CPC ..... A61K 31/519; A61K 31/517; A61K 45/06
See application file for complete search history.

(56) References Cited

U.S. PATENT DOCUMENTS 5,430,148 A    7/1995   Webber et al.

FOREIGN PATENT DOCUMENTS

| CN | 1706825 A | 12/2005 |
| GB | 14120 A | 4/1914 |
| GB | 982360 A | 2/1965 |
| RU | 2553343 C2 | 6/2015 |
| WO | WO 2009025760 A2 | 2/2009 |
| WO | 2017/029202 A1 | 2/2017 |

OTHER PUBLICATIONS

Nat Med, 2017; 23, 1113 (Year: 2017).*
Michel et al. Biomedicines. Feb. 2022; 10(2): 270 (Year: 2022).*
M. Thórólfsson, et al., L-Phenylalanine Binding and Domain Organization in Human Phenylalanine Hydroxylase: A Differential Scanning Calorimetry Study, Biochemistry, 2002, 41(24), 7573-7585.
F.H. Niesen, et al., The use of differential scanning fluorimetry to detect ligand interactions that promote protein stability, Nat. Protoc., 2007, 2(9), 2212-2221.
S.W. Gersting, et al., Pah/\(enu1) is a mouse model for tetrahydrobiopterin-responsive phenylalanine hydroxylase deficiency and promotes analysis of the pharmacological chaperone mechanism in vivo, Human Molecular Genetics, 2010, 19(10), 2039-2049.
S.W. Gersting, Activation of Phenylalanine Hydroxylase Induces Positive Cooperativity toward the Natural Cofactor, J. Biol. Chem., 2010, 285(40), 30686-30697.
Freyer M.W. and Lewis E.A., Isothermal Titration Calorimetry: Experimental Design, Data Analysis, and Probing Macromolecule/Ligand Binding and Kinetic Interactions, Methods in Cell Biology, 2008, vol. 4, Chapter 4, pp. 79-113.
Jaspreet Singh Kochhar, et al., Clinical therapeutics for phenylketonuria, Drug Deliv. and Transl. Res., 2012, 2(4), 223-237.
Gladys Ho, et al., Phenylketonuria: translating research into novel therapies, Transl. Pedatr., 2014, 3(2), 49-62.
Steinberg, Pablo, et al., Effect of triamterene on tyrosine hydroxylase activity, Naunyn-Schmiedebergs Arch. Pharmacol., 1984, 327(2), 119-123.
International Search Report for PCT/EP2020/053714 dated May 15, 2020.

* cited by examiner

Primary Examiner — Clinton A Brooks
Assistant Examiner — Jerica Katlynn Wilson
(74) Attorney, Agent, or Firm — Casimir Jones, S.C.; Tristan A. Fuierer

(57) ABSTRACT

The present invention relates to a compound selected from the group consisting of nolatrexed, triamterene, sultopride and hydrastinine or a pharmaceutically acceptable salt thereof, preferably triamterene, nolatrexed or a pharmaceutically acceptable salt thereof, and to combination of said compounds with other active ingredients, for use in the treatment and/or prevention of phenylketonuria, to the use of said compound or its combinations in the manufacture of a medicament for the treatment or prevention of said diseases and to a method of treating and/or preventing by administration of said compound or its combinations.

7 Claims, No Drawings

Specification includes a Sequence Listing.

```
                        SEQUENCE LISTING

<160> NUMBER OF SEQ ID NOS: 1

<210> SEQ ID NO 1
<211> LENGTH: 452
<212> TYPE: PRT
<213> ORGANISM: Homo sapiens

<400> SEQUENCE: 1

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
```

|   |   |   | 340 |   |   |   | 345 |   |   |   | 350 |   |   |
|---|---|---|---|---|---|---|---|---|---|---|---|---|---|
| Glu | Leu | Gln | Tyr | Cys | Leu | Ser | Glu | Lys | Pro | Lys | Leu | Leu | Pro | Leu | Glu |
|   |   | 355 |   |   |   |   | 360 |   |   |   |   | 365 |   |

Leu Glu Lys Thr Ala Ile Gln Asn Tyr Thr Val Thr Glu Phe Gln Pro
        370             375             380

Leu Tyr Tyr Val Ala Glu Ser Phe Asn Asp Ala Lys Glu Lys Val Arg
385             390             395             400

Asn Phe Ala Ala Thr Ile Pro Arg Pro Phe Ser Val Arg Tyr Asp Pro
            405             410             415

Tyr Thr Gln Arg Ile Glu Val Leu Asp Asn Thr Gln Gln Leu Lys Ile
        420             425             430

Leu Ala Asp Ser Ile Asn Ser Glu Ile Gly Ile Leu Cys Ser Ala Leu
        435             440             445

Gln Lys Ile Lys
    450

TRIAMTERENE OR NOLATREXED FOR USE IN THE TREATMENT OF PHENYLKETONURIA

CROSS-REFERENCE TO RELATED APPLICATIONS

This application is filed under the provisions of 35 U.S.C. § 371 and claims the priority of International Patent Application No. PCT/EP2020/053714 filed on 13 Feb. 2020 entitled "TRIAMTERENE OR NOLATREXED FOR USE IN THE TREATMENT OF PHENYLKETONURIA" in the name of Raúl INSA BORONAT, et al., which claims priority to European Patent Application No. 19382102.2, filed on 14 Feb. 2019, both of which are hereby incorporated by reference herein in their entirety.

FIELD OF THE INVENTION

The present invention relates to compounds for use in the treatment and/or prevention of phenylketonuria.

BACKGROUND OF THE INVENTION

Phenylketonuria (PKU), also known as phenylalanine hydroxylase deficiency, is a rare metabolic disorder characterized by impaired conversion of phenylalanine (Phe) to tyrosine (Tyr) and, thus, it increases the levels of phenylalanine in blood. Phenylalanine is an amino acid that is obtained through the diet, e.g. in proteins and in some artificial sweeteners. If PKU is left untreated, the resultant accumulation of excess blood phenylalanine can cause physiological, neurological and intellectual disabilities.

The signs and symptoms of PKU vary from mild to severe. The most severe form of this disorder is known as classic PKU. Infants with classic PKU appear normal until they are a few months old. Without treatment, these children develop permanent intellectual disability. Seizures, delayed development, behavioral problems and psychiatric disorders are also common. Less severe forms of this condition, sometimes called variant PKU and non-PKU hyperphenylalaninemia, have a smaller risk of brain damage. People with very mild cases may not require treatment with a low-phenylalanine diet.

Babies born from mothers who have PKU and uncontrolled phenylalanine levels have a significant risk of intellectual disability because they are exposed to very high levels of phenylalanine before birth. These infants may also have a low birth weight and grow more slowly than other children. Other characteristic medical problems include heart defects or other heart problems, microcephaly and behavioral problems. Women with PKU and uncontrolled phenylalanine levels also have an increased risk of pregnancy loss.

Mutations in the PAH gene cause phenylketonuria since this gene is responsible of the production of phenylalanine hydroxylase, which catalyzes the para-hydroxylation of phenylalanine to tyrosine. If gene mutations reduce the activity of phenylalanine hydroxylase, phenylalanine from the diet is not processed effectively. As a result, this amino acid can build up to toxic levels in the blood and other tissues. Because nerve cells in the brain are particularly sensitive to phenylalanine levels, excessive amounts of this substance can cause brain damage.

PKU may be classified as classic PKU (approximately 48% of cases), variant (or mild) PKU (approximately 24% of cases) and non-PKU HPA (or mild hyperphenylalaninemia (HPA)), which corresponds to approximately 16% of the cases.

Classic PKU, the most severe form of the disorder, occurs when phenylalanine hydroxylase activity is severely reduced or absent. Mutations in the PAH gene that allow the enzyme to retain some activity result in milder versions of this condition, such as variant PKU or non-PKU hyperphenylalaninemia.

Phenylketonuria is considered classic PKU when blood phenylalanine levels in untreated subjects are greater than 1200 µmol/L, variant PKU when blood phenylalanine levels in untreated subjects are comprised between 600-1200 µmol/L, and non-PKU hyperphenylalaninemia (or mild hyperphenylalaninemia) when blood phenylalanine levels in untreated subjects are comprised between 120-600 µmol/L.

Some PKU patients benefit from oral administration of BH4 (also known as (6R)-L-erythro-5,6,7,8-tetrahydrobiopterin or tetrahydrobiopterin, which is an essential cofactor in the hydroxylation of phenylalanine catalyzed by phenylalanine hydroxylase) in that their blood phenylalanine level decreases or even normalizes under pharmacological therapy with BH4. The frequency of BH4-responsiveness is highest in patients with non-PKU HPA, or mild PKU resulting from PAH mutations that allow for residual enzyme activity. Conversely, the response rate among patients with classic PKU is lower.

Since pharmacotherapy for PKU is still in early stages, treatment of PKU has predominantly been dietary manipulation, namely restriction of phenylalanine intake by decreasing the intake of natural protein and replacing it with a protein source devoid of phenylalanine or modified low-protein foods. This therapy is difficult to maintain throughout life, and dietary noncompliance is commonplace.

As to pharmacotherapy, sapropterin dihydrochloride, which is a synthetic preparation of the dihydrochloride salt of naturally occurring tetrahydrobiopterin (BH4), was the first pharmacologic agent for treatment of PKU and was approved by the FDA in 2007.

Large neutral amino acids (LNAA) have been proposed as a therapy for PKU based on their ability to block uptake of phenylalanine from the intestine and at the blood-brain barrier. Nevertheless, treatment with large neutral amino acids are contraindicated as monotherapy in pregnant women because it does not sufficiently lower blood phenylalanine levels to the range that is safe for fetal development.

Also, polyethyleneglycol-conjugated phenylalanine ammonia lyase (PEG-PAL) appears to be effective in lowering blood phenylalanine levels, but some immunologic reactions have been reported for this drug and it has to be administered as a daily subcutaneous injection. Nevertheless, in 2018 Palynziq (pegvaliase-pqpz), which is composed of recombinant phenylalanine ammonia lyase (rAvPAL) conjugated to N-hydroxysuccinimide (NHS)-methoxypolyethylene glycol, was approved by the FDA for adults with PKU.

Due to the small choice of pharmacological agents for the treatment of PKU and also to the side effects of the existing ones, there is a need for new pharmacological agents useful for the treatment of PKU.

SUMMARY OF THE INVENTION

The inventors have surprisingly found new pharmacological strategies for the treatment of phenylketonuria. These compounds have shown a positive effect on the activity of the phenylalanine hydroxylase enzyme in its stability and/or activity, both in the wild type and in a mutated enzyme (Arg261Gln, which is the most frequent mutation responsive to BH4).

Thus, in one aspect, the present invention relates to a compound selected from the group consisting of triamterene, nolatrexed, sultopride and hydrastinine or a pharmaceutically acceptable salt thereof, preferably triamterene, nolatrexed or a pharmaceutically acceptable salt thereof, for use in the treatment and/or prevention of phenylketonuria (PKU).

In another aspect, the invention relates to the use of a compound selected from the group consisting of triamterene, nolatrexed, sultopride and hydrastinine or a pharmaceutically acceptable salt thereof, preferably triamterene, nolatrexed or a pharmaceutically acceptable salt thereof, in the manufacture of a medicament for the treatment and/or prevention of phenylketonuria (PKU).

In another aspect, the invention also relates to a method of treating and/or preventing phenylketonuria (PKU) in a subject, comprising administering to said subject a therapeutically effective amount of a compound selected from the group consisting of triamterene, nolatrexed, sultopride and hydrastinine or a pharmaceutically acceptable salt thereof, preferably triamterene, nolatrexed or a pharmaceutically acceptable salt thereof.

In a further aspect, the present invention relates to a combination comprising one or more compounds selected from the group consisting of triamterene, nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof, for use in the treatment and/or prevention of phenylketonuria, wherein at least one compound is selected from the group consisting of triamterene, nolatrexed, sultopride and hydrastinine or a pharmaceutically acceptable salt thereof, preferably wherein at least one compound is selected from the group consisting of triamterene and nolatrexed or a pharmaceutically acceptable salt thereof.

In another aspect, the invention relates to the use of a combination comprising one or more compounds selected from the group consisting of triamterene, nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof, in the manufacture of a medicament for the treatment and/or prevention of phenylketonuria (PKU), wherein at least one compound is selected from the group consisting of triamterene, nolatrexed, sultopride and hydrastinine or a pharmaceutically acceptable salt thereof, preferably wherein at least one compound is selected from the group consisting of triamterene and nolatrexed or a pharmaceutically acceptable salt thereof.

In another aspect, the invention relates a method of treating and/or preventing phenylketonuria (PKU) in a subject, comprising administering to said subject a therapeutically effective amount of a combination comprising one or more compounds selected from the group consisting of triamterene, nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof, wherein at least one compound is selected from the group consisting of triamterene, nolatrexed, sultopride and hydrastinine or a pharmaceutically acceptable salt thereof, preferably wherein at least one compound is selected from the group consisting of triamterene and nolatrexed or a pharmaceutically acceptable salt thereof.

DESCRIPTION OF THE INVENTION

In the first aspect, the present invention relates to a compound selected from the group consisting of triamterene, nolatrexed, sultopride and hydrastinine or a pharmaceutically acceptable salt thereof, preferably triamterene, nolatrexed or a pharmaceutically acceptable salt thereof, for use in the treatment and/or prevention of phenylketonuria (PKU).

The invention also relates to the use of a compound selected from the group consisting of triamterene, nolatrexed, sultopride and hydrastinine or a pharmaceutically acceptable salt thereof, preferably triamterene, nolatrexed or a pharmaceutically acceptable salt thereof, in the manufacture of a medicament for the treatment and/or prevention of phenylketonuria (PKU).

The invention also relates to a method of treating and/or preventing phenylketonuria (PKU) in a subject, comprising administering to said subject a therapeutically effective amount of a compound selected from the group consisting of triamterene, nolatrexed, sultopride and hydrastinine or a pharmaceutically acceptable salt thereof, preferably triamterene, nolatrexed or a pharmaceutically acceptable salt thereof.

The invention also discloses a compound selected from the group consisting of bufuralol, valganciclovir, ricobendazole, albendazole, valacyclovir, minoxidil, and loxoribine, or a pharmaceutically acceptable salt thereof, for use in the treatment and/or prevention of phenylketonuria.

The invention also discloses the use of a compound selected from the group consisting of bufuralol, valganciclovir, ricobendazole, albendazole, valacyclovir, minoxidil, and loxoribine, or a pharmaceutically acceptable salt thereof, in the manufacture of a medicament for the treatment and/or prevention of phenylketonuria (PKU).

The invention also relates to a method of treating and/or preventing phenylketonuria (PKU) in a subject, comprising administering to said subject a therapeutically effective amount of a compound selected from the group consisting of bufuralol, valganciclovir, ricobendazole, albendazole, valacyclovir, minoxidil, and loxoribine, or a pharmaceutically acceptable salt thereof.

The terms "treating" and "treatment", as used herein, means reversing, alleviating, inhibiting the progress of, the disease or condition to which such term applies, or one or more symptoms of such disease or condition, such as lowering blood phenylalanine with respect to pretreatment levels.

The terms "preventing" and "prevention", as used herein, means avoiding or inhibiting the onset of one or more symptoms of the disease or condition to which such term applies, such as inhibiting rising of blood phenylalanine above 120 μmol/L.

Preferably, the compounds disclosed herein, are used for the treatment of PKU.

Triamterene or 2,4,7-triamino-6-phenylpteridine has the chemical structure depicted below.

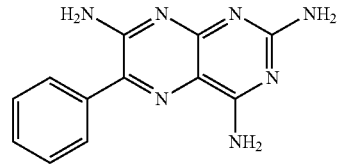 [SMILES: Nc1nc(N)c2nc(-c3ccccc3)c(N)nc2n1]

This compound has been developed as a diuretic agent. This compound is commercially available or may be synthesized using a suitable preparation method, such as that disclosed in GB 982360.

Nolatrexed or 2-amino-6-methyl-5-(4-pyridylthio)-4 (3H)-quinazolinone has the chemical structure depicted below.

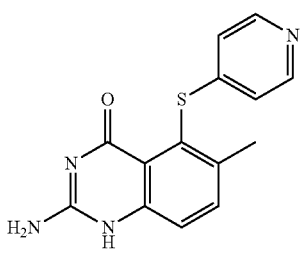 [SMILES: Cc1ccc2[nH]c(N)nc(=O)c2c1Sc1ccncc1]

This compound was developed as an antineoplastic agent, in particular for the treatment of hepatocellular carcinoma. This compound is commercially available or may be synthesized using a suitable preparation method, such as that disclosed in U.S. Pat. No. 5,430,148 (nolatrexed corresponds to compound 14A of this document).

Sultopride or N-[(1-ethyl-2-pyrrolidinyl)methyl]-5-(ethylsulfonyl)-o-anisamide has the chemical structure depicted below.

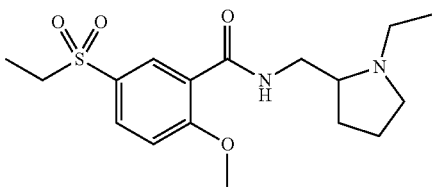 [SMILES: CCN1CCCC1CNC(=O)c1cc(S(=O)(=O)CC)ccc1OC]

This compound has been developed as an antidepressant. This compound is commercially available or may be synthesized using a suitable preparation method, such as that disclosed in CN1706825 A.

Hydrastinine or 6-methyl-7,8-dihydro-5H-[1,3]dioxolo[4,5-g]isoquinolin-5-ol has the chemical structure shown below.

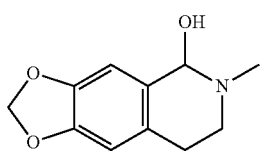

This compound has been developed as a cardiotonic and hemostatic agent. This compound is commercially available or may be synthesized using a suitable preparation method, such as that disclosed in GB 14120.

Bufuralol or 2-(tert-butylamino)-1-(7-ethyl-1-benzofuran-2-yl)ethan-1-ol has the chemical structure depicted below.

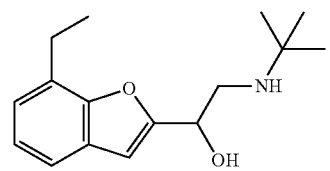 [SMILES: CCc1cccc2cc(C(O)CNC(C)(C)C)oc12]

This compound has been developed as a beta-adrenoceptor antagonist and is commercially available. This is preferably used as the hydrochloride salt. This compound may be used either in racemic form or as the (S)- or (R)-enantiomers, preferably the (S)-enantiomer.

Valganciclovir or [2-[(2-amino-6-oxo-3H-purin-9-yl) methoxy]-3-hydroxypropyl] (2S)-2-amino-3-methylbutanoate has the chemical structure depicted below.

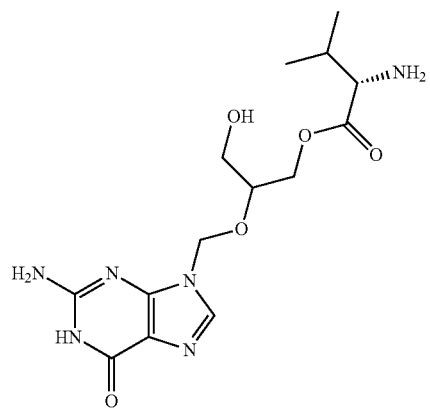 [SMILES: CC(C)[C@H](N)C(=O)OCC(CO)OCn1cnc2c(=O)[nH]c(N)nc21]

This compound has been developed as an antiviral medication used to treat cytomegalovirus infection in subjects with HIV/AIDS or following organ transplant and is commercially available. This compound is preferably used as the hydrochloride salt.

Ricobendazole or methyl [5-(propane-1-sulfinyl)-1H-benzoimidazol-2-yl]-carbamate has the chemical structure depicted below.

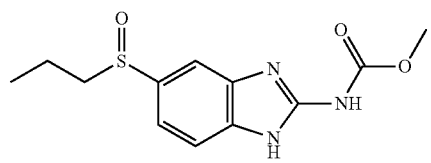 [SMILES: CCCS(=O)c1ccc2[nH]c(NC(=O)OC)nc2c1]

This compound has been developed as an anthelmintic and is commercially available. This compound is preferably used as the free base. Ricobendazole is one of the key metabolites of albendazole or (5-(propylthio)-1H-benzimidazol-2-yl)carbamic acid methyl ester. Albendazole has the chemical structure depicted below.

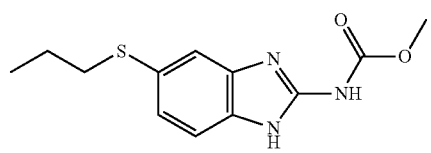 [SMILES: CCCSc1ccc2[nH]c(NC(=O)OC)nc2c1]

Albendazole has also been developed as an anthelmintic and is commercially available. This compound can be used as a prodrug of ricobendazole and is preferably used as the free base.

Valacyclovir or 2-[(2-amino-6-oxo-3H-purin-9-yl)methoxy]ethyl (2S)-2-amino-3-methylbutanoate has the chemical structure depicted below.

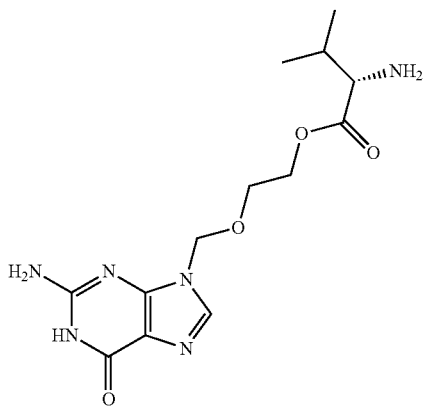 [SMILES: CC(C)[C@H](N)C(=O)OCCOCn1cnc2c(=O)[nH]c(N)nc21]

This compound has been developed as an antiviral medication used to treat herpes infection and is commercially available. This compound is preferably used as the hydrochloride salt.

Minoxidil or 2,6-diamino-4-(piperidin-1-yl)pyrimidine 1-oxide has the chemical structure depicted below.

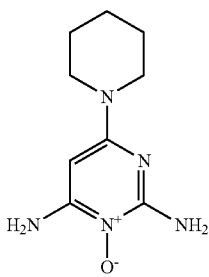 [SMILES: Nc1cc(N2CCCCC2)nc(N)[n+]1[O-]]

This compound has been developed for the treatment of hypertension and hair loss and is commercially available. This compound is preferably used as the free base.

Loxoribine or 2-amino-9-[(2R,3R,4S,5R)-3,4-dihydroxy-5-(hydroxymethyl)oxolan-2-yl]-7-prop-2-enyl-3H-purine-6,8-dione has the chemical structure depicted below.

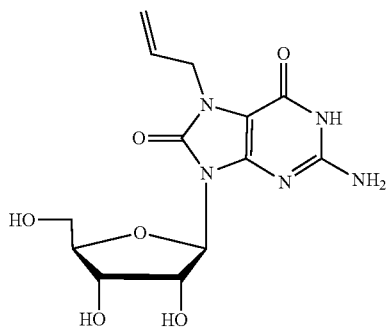

This compound has immunostimulatory and immunomodulatory activity and is commercially available. This compound is preferably used as the free base.

The term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

Further, the term "pharmaceutically acceptable salt" refers to any salt, which, upon administration to the recipient is capable of providing (directly or indirectly) a compound as described herein. For instance, a pharmaceutically acceptable salt of compounds provided herein may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, ammonium, and organic alkali salts such as, for example, ethylenediamine, ethanolamine, N,N-dialkylenethanolamine, triethanolamine, glucamine and basic aminoacids salts. Examples of the metallic salts include, for example, sodium, potassium, calcium, magnesium, aluminium and lithium salts.

In another particular embodiment, the compound for use according to the invention is triamterene or a pharmaceutically acceptable salt thereof, preferably triamterene (i.e. triamterene free base).

In a particular embodiment, the compound for use according to the invention is nolatrexed or a pharmaceutically acceptable salt thereof, preferably nolatrexed dihydrochloride.

In another particular embodiment, the compound for use according to the invention is sultopride or a pharmaceutically acceptable salt thereof, preferably sultopride hydrochloride.

In another particular embodiment, the compound for use according to the invention is hydrastinine or a pharmaceutically acceptable salt thereof, preferably hydrastinine hydrochloride.

In another particular embodiment, the phenylketonuria is selected from variant phenylketonuria, non-phenylketonuria (or mild) hyperphenylalaninemia, and classic phenylketonuria; preferably selected from variant phenylketonuria and non-phenylketonuria (or mild) hyperphenylalaninemia; even more preferably variant phenylketonuria.

In another particular embodiment of the various aspects of the present invention, subjects suffering from phenylketonuria express one or more variants of the PAH enzyme selected from the group consisting of R261Q, R408W, IVS10, E390G, D415N, R241H, I306V, L348V, V388M, R158Q, Y414C, A300S, R297H, L48S, I65T, V245A, V106A, A403V, E280K, R252W, P281L, S349P and IVS12; preferably R261Q, R408W, IVS10, E390G, D415N, R241H, I306V, L348V, V388M, R158Q, Y414C, A300S, R297H, L48S, I65T, V245A, V106A and IVS12; more preferably from the group consisting of R261Q, R408W, IVS10, E390G, D415N, R241H, I306V, L348V, V388M, R158Q, Y414C, A300S, R297H, L48S and I65T; even more preferably R261Q.

The nomenclature used for the above mutations is a first letter designating the amino acid (using the one-letter amino acid code) in the wild-type human PAH enzyme, a number designating its position in the wild-type human PAH enzyme amino acid sequence and the final letter designating the amino acid present at that position in the mutated PAH enzyme, e.g. R261Q means that arginine (R) at position 261 has been changed to glutamine (Q). R408W denotes that arginine (R) at position 408 has been changed to tryptophan (W). E390G denotes that glutamate (E) at position 390 has been changed to glycine (G). D415N denotes that aspartate (D) at position 415 has been changed to asparagine (N). R241H denotes that arginine (R) at position 241 has been changed to histidine (H). I306V denotes that isoleucine (I) at position 306 has been changed to valine (V). L348V denotes that leucine (L) at position 348 has been changed to valine (V). V388M denotes that valine (V) at position 388 has been changed to methionine (M). R158Q denotes that arginine (R) at position 158 has been changed to glutamine (Q). Y414C denotes that tyrosine (Y) at position 414 has been changed to cysteine (C). A300S denotes that alanine (A) at position 300 has been changed to serine (S). R297H denotes that arginine (R) at position 297 has been changed to histidine (H). L48S denotes that leucine (L) at position 48 has been changed to serine (S). I65T denotes that isoleucine (I) at position 65 has been changed to threonine (T). V245A denotes that valine (V) at position 245 has been changed to alanine (A). V106A denotes that valine (V) at position 106 has been changed to alanine (A). A403V denotes that alanine (A) at position 403 has been changed to valine (V). E280K denotes that glutamate (E) at position 280 has been changed to lysine (K). R252W denotes that arginine (R) at position 252 has been changed to tryptophan (W). P281L denotes that proline (P) at position 281 has been changed to leucine (L). S349P denotes that serine (S) at position 349 has been changed to proline (P).

The mutation IVS10 creates a novel splice acceptor site in intron 10 causing aberrant splicing that results in a transcript with 9 nucleotides inserted between the normal sequences of exon 10 and exon 11. This corresponds to a protein with three extra amino acids (Gly-Leu-Gln) that are inserted between residues Q355 and Y356.

The mutation IVS12 corresponds to a GT-to-AT substitution at the 5-prime splice donor site of intron 12 that results in the skipping of the preceding exon during RNA splicing. The corresponding messenger RNA shows an internal 116-base deletion corresponding precisely to exon 12 and leading to the synthesis of the truncated protein lacking the C-terminal 52 amino acids.

The wild-type human PAH enzyme has the following sequence, provided in the UniProt database under entry P00439 (version 237 from Dec. 11, 2019):

```
                                            (SEQ ID NO: 1)
MSTAVLENPGLGRKLSDFGQETSYIEDNCNQNGAISLIFSLKEEVGALAK

VLRLFEENDVNLTHIESRPSRLKKDEYEFFTHLDKRSLPALTNIIKILRH

DIGATVHELSRDKKKDTVPWFPRTIQELDRFANQILSYGAELDADHPGFK

DPVYRARRKQFADIAYNYRHGQPIPRVEYMEEEKKTWGTVFKTLKSLYKT

HACYEYNHIFPLLEKYCGFHEDNIPQLEDVSQFLQTCTGFRLRPVAGLLS

SRDFLGGLAFRVFHCTQYIRHGSKPMYTPEPDICHELLGHVPLFSDRSFA

QFSQEIGLASLGAPDEYIEKLATIYWFTVEFGLCKQGDSIKAYGAGLLSS

FGELQYCLSEKPKLLPLELEKTAIQNYTVTEFQPLYYVAESFNDAKEKVR

NFAATIPRPFSVRYDPYTQRIEVLDNTQQLKILADSINSEIGILCSALQK

IK
```

The compounds for use according to the invention may be administered by any appropriate route (via), such as, oral (e.g., oral, sublingual, etc.), parenteral (e.g., subcutaneous, intramuscular, intravenous, intramuscular, etc.), vaginal, rectal, nasal, topical, ophthalmic, etc., preferably oral or parenteral, more preferably oral.

In particular, the compounds for use according to the invention are administered as a pharmaceutical composition which comprises the corresponding (active) compound and one or more pharmaceutically acceptable excipients.

The term "pharmaceutically acceptable excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are known by the skilled person.

The pharmaceutically acceptable excipient necessary to manufacture the desired pharmaceutical composition of the invention will depend, among other factors, on the elected administration route. Said pharmaceutical compositions may be manufactured according to conventional methods known by the skilled person in the art.

The compounds for use according to the invention may be administered in a "therapeutically effective amount", i.e. a nontoxic but sufficient amount of the corresponding compound to provide the desired effect. The amount that is "effective" will vary from subject to subject, depending on the age and general condition of the individual, the particular compound administered, and the like. Thus, it is not always possible to specify an exact "therapeutically effective amount". However, an appropriate amount in any individual case may be determined by one of ordinary skill in the art using routine experimentation.

The compounds for use according to the invention will typically be administered once or more times a day, for example 1, 2, 3 or 4 times daily, with typical total daily doses depending on the particular compound and severity of the disease, and may be easily determined by the skilled practitioner. By way of example, typical total daily doses of sultopride or a pharmaceutically acceptable salt thereof are in the range of from 0.1 to 18000 mg/day (expressed as sultopride free base), preferably from 0.1 to 1800 mg/day, even more preferably from 1 to 1800 mg/day. Typical total daily doses of nolatrexed or a pharmaceutically acceptable salt thereof administered by oral route are in the range of from 0.2 to 14000 mg/day (expressed as nolatrexed free base), preferably from 0.2 to 1400 mg/day, even more preferably from 1 to 1400 mg/day. Typical total daily doses of nolatrexed or a pharmaceutically acceptable salt thereof administered by parenteral route are in the range of from 0.1 to 8000 mg/m$^2$/day (expressed as nolatrexed free base), preferably from 0.1 to 800 mg/m$^2$/day, even more preferably from 1 to 800 mg/m$^2$/day. Typical total daily doses of triamterene or a pharmaceutically acceptable salt thereof are in the range of from 0.1 to 10000 mg/day (expressed as triamterene free base), preferably from 0.1 to 300 mg/day, even more preferably from 1 to 300 mg/day. Typical total daily doses of hydrastine or a pharmaceutically acceptable salt thereof are in the range of from 0.1 to 5000 mg/day (expressed as hydrastine free base), preferably from 0.1 to 500 mg/day, even more preferably from 1 to 500 mg/day. Typical total daily doses of bufuralol or a pharmaceutically acceptable salt thereof are in the range of from 0.1 to 1200 mg/day (expressed as bufuralol free base), preferably from 0.1 to 120 mg/day, even more preferably from 1 to 120 mg/day. Typical total daily doses of valganciclovir or a pharmaceutically acceptable salt thereof are in the range of from 0.1 to 18000 mg/day (expressed as valganciclovir free base), preferably from 0.1 to 1800 mg/day, even more preferably from 1 to 1800 mg/day. Typical total daily doses of albendazole or ricobendazole or a pharmaceutically acceptable salt thereof are in the range of from 0.1 to 4000 mg/day (expressed as ricobendazole or albendazole free base), preferably from 0.1 to 400 mg/day, even more preferably from 1 to 400 mg/day. Typical total daily doses of valacyclovir or a pharmaceutically acceptable salt thereof are in the range of from 0.1 to 20000 mg/day (expressed as valacyclovir free base), preferably from 0.1 to 2000 mg/day, even more preferably from 1 to 2000 mg/day. Typical total daily doses of minoxidil or a pharmaceutically acceptable salt thereof are in the range of from 0.1 to 1000 mg/day (expressed as minoxidil free base), preferably from 0.1 to 100 mg/day, even more preferably from 1 to 100 mg/day. Typical total daily doses of loxoribine or a pharmaceutically acceptable salt thereof are in the range of from 0.1 to 100 mg/day (expressed as loxoribine free base), preferably from 0.1 to 10 mg/day, even more preferably from 1 to 10 mg/day.

The pharmaceutical compositions may be prepared using standard methods such as those described or referred to in the Spanish and US Pharmacopoeias and similar reference texts.

The term "subject" refers to a mammal, e.g., a human.

The compounds for use according to the invention may be administered as the sole active ingredient or in combination with other active ingredients. In a particular embodiment, the compounds are used as the sole active ingredient. In another particular embodiment, the compounds are used in combination with other active ingredients.

In another aspect, the present invention relates to a combination comprising one or more compounds selected from the group consisting of triamterene, nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof, for use in the treatment and/or prevention of phenylketonuria, wherein at least one compound is selected from the group consisting of triamterene, nolatrexed, sultopride and hydrastinine or a pharmaceutically acceptable salt thereof, preferably wherein at least one compound is selected from the group consisting of triamterene and nolatrexed or a pharmaceutically acceptable salt thereof.

The invention also relates to the use of a combination comprising one or more compounds selected from the group consisting of triamterene, nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof, in the manufacture of a medicament for the treatment and/or prevention of phenylketonuria (PKU), wherein at least one compound is selected from the group consisting of triamterene, nolatrexed, sultopride and hydrastinine or a pharmaceutically acceptable salt thereof, preferably wherein at least one compound is selected from the group consisting of triamterene and nolatrexed or a pharmaceutically acceptable salt thereof.

The invention also relates a method of treating and/or preventing phenylketonuria (PKU) in a subject, comprising administering to said subject a therapeutically effective amount of a combination comprising one or more compounds selected from the group consisting of triamterene, nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof, wherein at least one compound is selected from the group consisting of triamterene, nolatrexed, sultopride and hydrastinine or a pharmaceutically acceptable salt thereof, preferably wherein at least one compound is selected from the group consisting of triamterene and nolatrexed or a pharmaceutically acceptable salt thereof.

The term "combination" refers to a product comprising one or more of the defined compounds, either in a single composition or in several compositions (or units), in which case the corresponding compounds are distributed among the several compositions. Preferably, the combination refers to several compositions, in particular comprising one composition (or unit) per compound (compound as defined above) of the combination. The expression "one or more" when characterizing the combination refers to at least one, preferably 1, 2, 3, 4, or 5 compounds, more preferably, 1, 2 or 3 compounds, even more preferably 1 or 2 compounds.

When the combination is in the form of a single composition, the compounds present in the combination are always administered simultaneously.

When the combination is in the form of several compositions (or units), each of them having at least one of the compounds of the combination, the compositions or (units) may be administered simultaneously, sequentially or separately.

Simultaneous administration means that the compounds or compositions (or units) are administered at the same time.

Sequential administration means that the compounds or compositions (or units) are administered at different time points in a chronologically staggered manner.

Separate administration means that the compounds or compositions (or units) are administered at different time points independently of each other.

Triamterene, nolatrexed, sultopride, hydrastinine, bufuralol, valganciclovir, ricobendazole, albendazole, valacyclovir, minoxidil, loxoribine including their pharmaceutically acceptable salts have been described in detail above.

Sapropterin or (−)-(6R)-2-amino-6-((1R,2S)-1,2-dihydroxypropyl)-5,6,7,8-tetrahydro-4(3H)-pteridinone has the chemical structure depicted below.

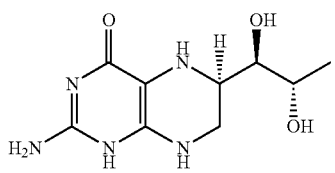 [SMILES: C[C@H](O)[C@H](O)[C@H]1CNc2[nH]c(N)nc(=O)c2N1]

This compound has been developed for the treatment of hyperphenylalaninaemia in patients with PKU and/or tetrahydrobiopterin deficiency and is commercially available. This compound is preferably used as the hydrochloride salt, in particular the dihydrochloride salt.

Sepiapterin or S-(−)-2-amino-7,8-dihydro-6-(2-hydroxy-1-oxopropyl)-4(1H)-pteridinone has the chemical structure depicted below.

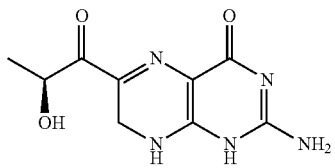 [SMILES: C[C@H](O)C(=O)C1=Nc2c([nH]c(N)nc2=O)NC1]

This compound is a stable precursor of tetrahydrobiopterin and is intracellularly converted to said compound. This compound is commercially available. Sepiapterin is preferably used as the free base.

Oxitriptan or (2S)-2-amino-3-(5-hydroxy-1H-indol-3-yl) propanoic acid has the chemical structure depicted below.

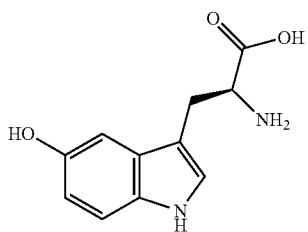 [SMILES: N[C@@H](Cc1c[nH]c2ccc(O)cc12)C(=O)O]

This compound is commercially available and is used for the treatment of PKU in some markets (Taiwan). Oxitriptan is currently under development as an antidepressant and appetite suppressant.

Pyrimethamine or 5-(4-chlorophenyl)-6-ethylpyrimidine-2,4-diamine has the chemical structure depicted below

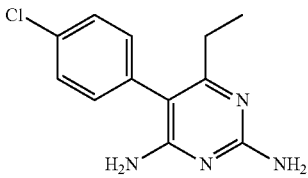 [SMILES: CCc1nc(N)nc(N)c1-c1ccc(Cl)cc1]

This compound is an antiparasitic compound used to treat toxoplasmosis and is commercially available. It had been previously used for malaria, but has been shown to have some effects in the treatment of PKU. This compound is preferably used as the free base.

Pegvaliase is a PEGylated recombinant phenylalanine ammonia lyase that converts phenylalanine to the harmless metabolites trans-cinnamic acid and ammonia, reducing the levels of phenylalanine. This product is used for the treatment of PKU and is commercially available.

The combination comprises at least one compound that is selected from the group consisting of triamterene, nolatrexed, sultopride and hydrastinine or a pharmaceutically acceptable salt thereof, preferably at least one compound that is selected from the group consisting of triamterene and nolatrexed or a pharmaceutically acceptable salt thereof.

In a preferred embodiment, the combination comprises at least triamterene or a pharmaceutically acceptable salt thereof, preferably triamterene (i.e. triamterene free base). Accordingly, the combination comprises triamterene or a pharmaceutically acceptable salt thereof (preferably triamterene free base) and one or more (preferably one) compounds selected from nolatrexed, sultopride, hydrastinine, bufuralol, valganciclovir, ricobendazole, albendazole, valacyclovir, minoxidil, loxoribine, sapropterin, sepiapterin, oxitriptan, pyrimethamine pegvaliase, or a pharmaceutically acceptable salt thereof.

In another preferred embodiment, the combination comprises at least nolatrexed or a pharmaceutically acceptable salt thereof, preferably nolatrexed dihydrochloride. Accordingly, the combination comprises nolatrexed or a pharmaceutically acceptable salt thereof (preferably nolatrexed dihydrochloride) and one or more (preferably one) compounds selected from triamterene, sultopride, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof.

In another preferred embodiment, the combination comprises at least sultopride or a pharmaceutically acceptable salt thereof, preferably sultopride hydrochloride. Accordingly, the combination comprises sultopride or a pharmaceutically acceptable salt thereof (preferably sultopride hydrochloride) and one or more (preferably one) compounds selected from triamterene, nolatrexed, hydrastinine, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof.

In another preferred embodiment, the combination comprises hydrastinine or a pharmaceutically acceptable salt thereof, preferably hydrastinine hydrochloride. Accordingly, the combination comprises hydrastinine or a pharmaceutically acceptable salt thereof (preferably hydrastinine hydrochloride) and one or more (preferably one) compounds selected from triamterene, nolatrexed, sultopride, bufuralol, valganciclovir, ricobendazole, albendazole, valacyclovir, minoxidil, loxoribine, sapropterin, sepiapterin, oxitriptan, pyrimethamine, pegvaliase, or a pharmaceutically acceptable salt thereof.

In particular, the combinations for use according to the invention are administered as pharmaceutical compositions, which comprise the corresponding (active) compounds and a pharmaceutically acceptable excipient, as previously defined.

The combinations for use according to the invention will typically be administered once or more times a day, for example 1, 2, 3 or 4 times daily, with typical total daily doses depending on the particular compound and severity of the disease, and may be easily determined by the skilled practitioner.

The compounds and combinations for use according to the present invention are preferably use in conjunction with a phenylalanine-restricted diet, wherein the intake of phenylalanine is partially or totally removed, by restricting natural protein and providing instead a protein substitute that lacks phenylalanine but is enriched in tyrosine.

In a preferred embodiment, the phenylketonuria is selected from variant phenylketonuria, non-phenylketonuria (or mild) hyperphenylalaninemia, and classic phenylketonuria; preferably selected from variant phenylketonuria and non-phenylketonuria (or mild) hyperphenylalaninemia; even more preferably variant phenylketonuria.

In a particular embodiment, subjects suffering from phenylketonuria express one or more variants of the PAH enzyme selected from the group consisting of R261Q, R408W, IVS10, E390G, D415N, R241H, I306V, L348V, V388M, R158Q, Y414C, A300S, R297H, L48S, I65T, V245A, V106A, A403V, E280K, R252W, P281L, S349P and IVS12; preferably R261Q, R408W, IVS10, E390G, D415N, R241H, I306V, L348V, V388M, R158Q, Y414C, A300S, R297H, L48S, I65T, V245A, V106A and IVS12; more preferably from the group consisting of R261Q, R408W, IVS10, E390G, D415N, R241H, I306V, L348V, V388M, R158Q, Y414C, A300S, R297H, L48S and I65T; even more preferably R261Q. Said variants are as previously defined.

The following examples represent specific embodiments of the present invention. They do not intend to limit in any way the scope of the invention defined in the present description.

EXAMPLES

Materials and Methods

1. Thermal Stability Shift Assay

Thórólfsson et al. (Biochemistry, 2002, 41(24), 7573-7585) describe that the thermal denaturation of hPAH occurs in three stages: (i) unfolding of the four regulatory domains, which is responsible for the low-temperature calorimetric transition (ii) unfolding of two (out of the four) catalytic domains, which is responsible for the high-temperature transition; and (iii) irreversible protein denaturation. The most important domain for stabilization is the regulatory domain.

Thus, to test the compound effect on thermal stability of the target protein a thermal stability shift assay (also called differential scanning fluorimetry (DSF)) was performed [Niesen F. H. et al., Nat Protoc., 2007, 2(9), 2212-2221; Gersting S. W. et al., Human Molecular Genetics, 2010, 19(10), 2039-2049; and Gersting S. W. et al., J. Biol Chem. 2010, 285(40), 30686-30697]. DSF monitors thermal unfolding of proteins in the presence of a fluorescent dye (SYPRO Orange; $\lambda exc=465$ nm, $\lambda em=610$ nm) and was performed using a real-time PCR instrument (Applied BioSystems 7000HT Fast Real-Time PCR System). Compounds that increase the midpoints of thermal denaturation (Tm) are considered to bind and stabilize the protein.

In brief, purified wild-type or Arg261Gln (which is the most frequent mutation responsive to BH4) PAH proteins (diluted in 20 mM NaHEPES, pH 7.0 and 200 mM NaCl, 2 mM DTT to 2 mg/ml) were used at a final concentration of 0.2 mg/ml protein per sample. The compounds were tested at a final concentration of 30 µM. A no compound control (NCC) was used according to the compound solvent at a final concentration of 2% (H$_2$O, DMSO, ethanol, methanol). As a positive control we used the natural cofactor 6R-L-erythro-5,6,7,8-tetrahydrobiopterin (BH4, CAS 69056-38-8) stabilized in 100 mM dithiothreitol (DTT), in a final concentration of 43 µM. To exclude unspecific effects of the compound to the dye, a no protein control (NPC) was added (buffer, compound, dye). The measurement was performed in duplicates and samples were denatured by scanning a temperature range of 20 to 75° C. at a scan rate of 0.5° C./min.

The data was normalized and the respective $T_m$ values were calculated by bi-phasic equation to determine temperatures at which half denaturation occurred (Software GraphPadPrism). To identify compound specific effects on the thermal stability of the target protein, the reference $T_m$ (NCC) was used to calculate the temperature shift between compound treated and not treated protein ($T_m-T_{mNCC}$), from duplicates, to provide transition midpoints shifts ($\Delta T_{m1}$ and $\Delta T_{m2}$). $T_{m1}$ and $T_{m2}$ are the two different transition mid point of the unfolding process of the protein as the tetrameric protein PAH unfolds in two steps due to its domains. A shift in $T_{m1}$ of 2° C. reflects a relevant increase in thermal stability on the regulatory domain and, thus, is considered a positive result.

2. Phenylalanine Hydroxylase Enzyme Activity Assay

This assay was completed in cell culture to analyze the enzyme activity in the presence of compounds. In brief, wild-type or Arg261Gln PAH constructs were transiently expressed in COS7-cells in a 96 well format reflecting the PAH genotype (COS7 cell line has no endogenous PAH). Cells were treated with the compounds at a final concentration of 10 µM and the enzyme activity of PAH was analyzed 48 h after transfection. The effect of the compounds on the residual enzyme activity was determined in comparison to non-treated cells (NCC, only compound solvent final 0.1%). To normalize the cellular background signal non transfected cells (NT control) were treated with compound or solvent equally for 48 h. As a positive control we used sepiapterin, a stable precursor of BH4 (CAS 17094-01-8), stabilized in 100 mM DTT, in a final concentration of 5 µM.

PAH activities were assayed at 25° C. as previously described (Gersting, S. W., J. Biol. Chem., 2010, 285(40), 30686-30697) with modifications. The standard mixture contained 22.35 mM NaHepes, pH 7.0, 2U/µl mg/mL catalase, 10 µM ferrous ammonium sulphate, and 1 mM L-Phe (L-phenylalanine) final. Assay mixture and cell culture enzyme were pre-incubated for 5 min and the reaction was initiated by the addition of 75 µM BH4 (stabilized in 100 mM dithiothreitol) final, run for 60 min and stopped by acetic acid. The amount of L-tyrosine production was measured and quantified by HPLC, assayed as triplicates.

The effect of compound on PAH enzyme activity was calculated from triplicates as follows: first the background of the NT cells were subtracted from the transfected cells (treated or NCC) and then the percentage of treated (compound) versus NCC was determined. Enzyme activity greater than 100% represents an increase in the enzyme activity with respect to NCC.

The HPLC was performed using the following experimental conditions:
1) Equipment:
HPLC: UltiMate 3000 (Dionex)
   Column: ODS-2 Hypersil™; 50×4.6 mm; particle size 3 µm; Thermo Scientific (Cat. No. 31603-054630)
   Pre-columns: Accucore XL C18, 4 µm, 10×4 mm; Thermo Scientific (Cat. No. 74104-014001)
2) PAH HPLC Running Buffer (pH 4.6):
   15.7 ml NH$_3$, 20 ml acetic acid, adjust with deionized H$_2$O to 1 L (if necessary adjust the pH with acetic acid)
3) Tyrosine Standards:
   60 µM, 30 µM, 15 µM, 7.5 µM, 3.75 µM Tyrosine in 0.1 M HCl 4) Running Conditions:
Fluorescence Detection of tyrosine: excitation 275 nm, emission 305 nm using UltiMate 3000 RS Fluorescence Detector (Dionex)
Eluent: PAH HPLC Running Buffer
Flow: 2 ml/min
Length of the run (standards): 1 min
Length of the run (PAH sample): 2.5 min
Elution of the tyrosine peak: app. 0.7 min
During the run the samples are kept at 4° C. in the Autosampler.
Column compartment is kept at 25° C.

3. Phenylalanine Hydroxylase Residual Protein Amount

The analysis of the residual PAH protein amount was based on the method described in Gersting S. W. et al., Human Molecular Genetics, 2010, 19(10), 2039-2049 with modifications.

Detection of the residual PAH protein amount was performed as a dot blot using the lysates obtained from the cell culture where transiently transfected COS-7 cells (with wild-type PAH or PAH variant) were exposed for 48 h to compounds. The experiment was carried out from the same samples as used for measuring enzyme activities.

2 µl of the lysate were dropped onto the nitrocellulose membrane. The membrane was allowed to air dry at room temperature for 30 min followed by 40 min blocking in 5% milk in TBS-Tween (room temperature). The membrane was incubated with the mouse monoclonal primary antibody specific for PAH (Millipore, Cat. No. MAB5278, 1:1000 dilution in 5% milk in TBS-Tween) for overnight at 4° C. Next, the membrane was washed (3×10 min in TBS-Tween) and incubated with the secondary HRP-conjugated antibody (anti-mouse antibody; Santa Cruz Biotechnology, Inc., Cat. No. sc-2005; 1:1000 dilution in 5% milk in TBS-Tween) followed by thorough washing in TBS-Tween (3×10 min) and distilled water (1×10 min). Blots were visualized with Pierce™ ECL substrate (ThermoFisher Scientific, Cat No. 32106) and chemiluminescence was monitored with a DIANA III Imaging system or ChemiDoc™ MP Imaging System (BioRad). To analyze the compound effect on the PAH protein amount densitometry analysis was performed using ImageJ Software.

The effect of compound on PAH protein amount was calculated from triplicates. As for determination of the enzyme activity the background of the not transfected cells (NT) was subtracted from the transfected cells (NCC or compound treated). In the next step delta of the NCC versus compound treated cells was calculated. Residual protein amount greater than 100% represents an increase in the stability of the enzyme with respect to NCC.

4. Isothermal Titration Calorimetry

Isothermal titration calorimetry (ITC) is a quantitative physical technique used to determine binding affinities of small molecules to proteins or other larger molecules [Freyer M. W. and Lewis E. A., *Methods in Cell Biology*, 2008, vol. 4, Chapter 4, pages 79-113]. The measurement detects changes of heat generated or absorbed when molecules interact, generate binding kinetics and thermodynamic profile of the molecular interaction. The following parameters are determined: KD (equilibrium dissociation constant), N (stoichiometry of the interaction (mol ligand/mol complex)), ΔH (enthalpy change), ΔG (Gibbs energy), T (temperature) and ΔS (entropy change).

ITC experiments were performed at 25° C. using a MicroCal PEAQ-ITC microcalorimeter (Malvern). PAH proteins were prepared in a HEPES buffer (HEPES 20 mM Hepes, 0.2M NaCl, 1 mM DTT, pH 7.0) containing 5% DMSO, in order to match the final DMSO concentration of the compounds dilutions. The protein concentration used (30 µM) was determined using ultraviolet (UV) absorbance at 280 nm. The compounds (500 mM) were prepared using the exact same buffer. Twelve injections of 3 µL of compound/ligand were titrated into the sample cell (containing the protein) over 31 min with a stirring speed of 750 rpm. Data was baseline adjusted by subtracting the background obtained from equivalent injections of compound into the buffer solution. The titration curves were analyzed using MicroCal PEAQ-ITC analytics software (version 1.1.0.1262, Malvern Instruments Ltd.) using a model that assumes a set of identical binding sites where the total heat of the solution is calculated as:

$$Q = \frac{nM_t \Delta H V_0}{2} \left[ 1 + \frac{X_t}{nM_t} + \frac{1}{nKM_t} - \sqrt{\left(1 + \frac{X_t}{nM_t} + \frac{1}{nKM_t}\right)^2 - \frac{4M_t}{nM_t}} \right]$$

where n is the number of binding sites, $M_t$ is the total protein concentration in the cell, ΔH is the molar heat of ligand binding, $X_t$ is the total concentration of ligand, and K the binding constant (K=1/KD). The heat released per injection (i), ΔQ(i), is calculated following the equation below, which compensates for the volume that is added in each injection (ΔVi). $V_0$ is the initial volume in the cell.

$$\Delta Q(i) = Q(i) + \frac{dV_i}{V_0}\left[\frac{Q(i) + Q(i-1)}{2}\right] - Q(i-1)$$

The parameters, n, K, and ΔH are determined using non-linear square fitting using the Levenberg-Marquardt algorithm.

5. Test Compounds

Triamterene (Santa Cruz Biotechnology), nolatretex dihycrochloride (Carbosynth), sultopride hydrochloride (Carbosynth), hydrastinine hydrochloride (Sant Cruz Biotechnology), bufuralol hydrochloride (Santa Cruz Biotechnology), S-bufuralol hydrochloride (Santa Cruz Biotechnology), ricobendazole (Santa Cruz Biotechnology), loxoribin (Tocris, Biogen), valganciclovir hydrochloride (Santa Cruz Biotechnology), valacyclovir hydrochloride (Santa Cruz Biotechnology) and minoxidil (Sigma Aldrich) were tested according one or more of the assays described above. Sepiapterin (Santa Cruz Biotechnology) or BH4 (Carbosynth) were used as the reference compounds.

Results

Example 1. Thermal Stability Shift Assay

Shifts in transition midpoints 1 and 2 ($\Delta T_{m1}$ and $\Delta T_{m2}$) of compound treated (30 µM) target proteins wild-type PAH (WT PAH) and Arg261Gln (R261Q PHA) were determined. 6R-L-erythro-5,6,7,8-tetrahydrobiopterin (BH4) (43 µM) was used as a positive control. The results are shown in the table below.

|  | WT PAH | | R261Q PAH | |
| --- | --- | --- | --- | --- |
| Compound | $\Delta T_{m1}$ | $\Delta T_{m2}$ | $\Delta T_{m1}$ | $\Delta T_{m2}$ |
| Bufuralol HCl | 1.62 | −0.09 | 2.24 | — |
| S-Bufuralol HCl | 1.05 | 0.24 | 3.73 | 0.92 |

-continued

| Compound | WT PAH ΔT$_{m1}$ | WT PAH ΔT$_{m2}$ | R261Q PAH ΔT$_{m1}$ | R261Q PAH ΔT$_{m2}$ |
|---|---|---|---|---|
| Ricobendazole | −0.48 | 2.57 | 2.19 | 3.39 |
| Triamterene | 0.33 | 3.23 | 2.21 | 2.82 |
| Loxoribine | 3.57 | — | — | — |
| Hydrastinine HCl | −0.49 | 6.10 | 2.46 | 0.04 |
| BH4 | 0.20 | 1.88 | 2.54 | 12.17 |

The results show that these compounds are able to stabilize the enzyme with a similar potency as the natural cofactor BH4, which shows higher stabilization activity on the mutant PAH than on the wild type protein in the thermal stability studies. For the application as a PKU treatment, the most relevant results are those on the mutant protein and in particular on the stabilization of the regulatory domain (Tm1).

Example 2. Phenylalanine Hydroxylase Enzyme Activity Assay

Compound effects on PAH enzyme activity in cells transiently expressing wild-type PAH (WT PAH) or Arg261Gln (R261Q) for 48 h were determined. The results are shown in the table below. Data represents the mean and the standard deviation (SD) of percentage of L-Tyrosine formation of compound treated cells (10 μM) compared to non-treated cells (NCC). Sepiapterin (5 μM) was used as a positive control.

| | | WT PAH Mean [% NCC] | WT PAH SD [% NCC] | R261Q PAH Mean [% NCC] | R261Q PAH SD [% NCC] |
|---|---|---|---|---|---|
| Nolatrexed 2HCl | | 284.15 | 55.25 | 531.60 | 52.69 |
| Triamterene | | 118.98 | 2.13 | 161.48 | 32.08 |
| Sultopride HCl | | 104.71 | 11.29 | 131.23 | 21.70 |
| Sepiapterin | | 297.14 | 9.76 | 2089.79 | 44.50 |

The results show that treatment with the above compounds significantly increases the enzymatic activity of wild type and mutant PAH expressed in COS7 cells, albeit at a lower extent than sepiapterin, used as positive control.

Example 3. Phenylalanine Hydroxylase Residual Protein Amount

Compound effects on PAH protein level in cells transiently expressing wild-type PAH (WT PAH) or Arg261Gln (R261Q) for 48 h were determined. The results are provided in the table below. Data represents the mean and the standard deviation (SD) of percentage of PAH immune blot signal of compound treated cells (10 μM) compared to non-treated cells (NCC). Sepiapterin (5 μM) was used as a positive control.

| Experiment | Compound | WT PAH Mean [% NCC] | WT PAH SD [% NCC] | R261Q PAH Mean [% NCC] | R261Q PAH SD [% NCC] |
|---|---|---|---|---|---|
| 1 | Valganciclovir HCl | 138.45 | 29.29 | 141.23 | 7.76 |
| 1 | Ricobendazole | 153.70 | 21.55 | 104.50 | 25.91 |
| 1 | Valacyclovir HCl | 146.25 | 10.26 | 103.81 | 10.15 |
| 1 | Minoxidil | 126.74 | 14.05 | 96.11 | 4.07 |
| 1 | Hydrastine HCl | 164.12 | 27.62 | 141.21 | 16.23 |
| 1 | Sepiapterin | 87.02 | 16.17 | 238.55 | 55.98 |
| 2 | Nolatrexed 2HCl | 108.45 | 4.93 | 255.58 | 15.87 |
| 2 | Triamterene | 110.05 | 4.34 | 129.86 | 9.45 |
| 2 | Sepiapterin | 106.44 | 8.45 | 310.19 | 20.09 |

The results show that treatment with the above compounds significantly increases the protein levels of wild type and mutant PAH expressed in COST cells, suggesting an increase on PAH protein stability or on protein synthesis.

Example 4. Isothermal Titration Calorimetry

Isothermal calorimetry data and analysis for titration of triamterene and hydrastinine hydrochloride to wild-type PAH (WT PAH) were performed. BH4 was used as a positive control. The results are shown in the table below.

| Compound | KD (μM) | N (sites) | ΔH (kJ/mol) | ΔG (kJ/mol) | −TΔS (kJ/mol) |
|---|---|---|---|---|---|
| Triamterene | 3.03 ± 0.00 | 0.726 ± 0.00 | −23.2 ± 0.7 | −31.5 | −8.32 |
| Hydrastinine HCl | 2.99 ± 3.2 | 1.310 ± 0.2 | 9.58 ± 2.3 | −31.6 | −41.1 |
| BH4 | 40.7 ± 14.1 | 0.936 ± 0.3 | −74.9 ± 33.1 | −25.1 | 49.8 |

The results show that triamterene and hydrastinine hydrochloride bind with high affinity to recombinant PAH, with a Kd in the low micromolar range.

The invention claimed is:

1. A method of treating and/or preventing phenylketonuria (PKU) in a subject, comprising administering to said subject a therapeutically effective amount of a compound selected from the group consisting of triamterene, nolatrexed, a pharmaceutically acceptable salt of triamterene, and a pharmaceutically acceptable salt of nolatrexed.

2. The method according to claim 1, wherein the phenylketonuria is selected from variant phenylketonuria, non-phenylketonuria hyperphenylalaninemia and classic phenylketonuria.

3. The method according to claim 2, wherein the phenylketonuria is variant phenylketonuria.

4. A method according to claim 1, wherein the compound comprises triamterene or a pharmaceutically acceptable salt thereof.

5. A method according to claim 4, wherein the compound comprises triamterene.

6. A method according to claim 1, wherein the compound comprises nolatrexed or a pharmaceutically acceptable salt thereof.

7. A method according to claim 6, wherein the compound comprises nolatrexed dihydrochloride.

* * * * *